US010695529B2

(12) United States Patent
Ramaprakash et al.

(10) Patent No.: US 10,695,529 B2
(45) Date of Patent: Jun. 30, 2020

(54) METHODS, SYSTEMS, AND APPARATUS FOR CONFIGURING COGNITIVE STATES (71) Applicant: Intel Corporation, Santa Clara, CA (US)

(72) Inventors: Nishanth Ramaprakash, Bangalore (IN); Sreenidhi Koti, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 266 days.

(21) Appl. No.: 15/690,556

(22) Filed: Aug. 30, 2017

(65) Prior Publication Data
US 2019/0060605 A1    Feb. 28, 2019

(51) Int. Cl.
*A61M 21/02* (2006.01)
*A61M 21/00* (2006.01)

(52) U.S. Cl.
CPC ....... *A61M 21/02* (2013.01); *A61M 2021/005* (2013.01); *A61M 2021/0027* (2013.01); *A61M 2205/3303* (2013.01); *A61M 2205/50* (2013.01); *A61M 2230/10* (2013.01)

(58) Field of Classification Search
CPC .............................................. A61M 21/00–02
See application file for complete search history.

(56) References Cited

U.S. PATENT DOCUMENTS

| 2006/0252979 | A1* | 11/2006 | Vesely | A61B 5/486 600/27 |
| 2013/0177883 | A1* | 7/2013 | Barnehama | G09B 5/00 434/236 |
| 2014/0343354 | A1* | 11/2014 | Larson | A61B 5/4812 600/28 |
| 2015/0038776 | A1* | 2/2015 | Donnet | A61M 21/00 600/28 |

(Continued)

*Primary Examiner* — Thaddeus B Cox
(74) *Attorney, Agent, or Firm* — Hanley, Flight & Zimmerman, LLC (57) ABSTRACT Methods, systems, and apparatus for changing a cognitive state of a user are disclosed. An example system includes a sensor to gather first electroencephalographic data from the user and an analyzer to determine a first cognitive state of the user based on the first electroencephalographic data and to determine a first binaural beat to present to the user based on the first cognitive state and a second cognitive state. The example system also includes an output to present the first binaural beat to the user. The sensor is to gather second electroencephalographic data from the user exposed to the first binaural beat. The analyzer is to determine a first effectiveness of the first binaural beat to place the user in the second cognitive state, and to determine a second binaural beat to present to the user based on the first cognitive state, the second cognitive state, and the second electroencephalographic data. The output is to present the second binaural beat to the user. In addition, the analyzer to determine a second effectiveness of the second binaural beat to place the user in the second cognitive state, to perform a comparison of the first effectiveness and the second effectiveness, and to (Continued)

select one of the first binaural beat or the second binaural beat for future presentation to the user to change the cognitive state of the user to the second cognitive state based on the comparison.

18 Claims, 5 Drawing Sheets

(56) References Cited

U.S. PATENT DOCUMENTS

| | | | | |
|---|---|---|---|---|
| 2015/0297109 | A1* | 10/2015 | Garten | A61B 5/04845 |
| | | | | 600/544 |
| 2016/0030702 | A1* | 2/2016 | Yang | A61B 90/361 |
| | | | | 600/28 |
| 2017/0286536 | A1* | 10/2017 | Rando | A61B 5/02416 |
| 2018/0344968 | A1* | 12/2018 | Gordon | A61M 21/02 |

\* cited by examiner

METHODS, SYSTEMS, AND APPARATUS FOR CONFIGURING COGNITIVE STATES

FIELD OF THE DISCLOSURE

This disclosure relates generally to cognitive states of brains, and, more particularly, to methods, systems, and apparatus for configuring cognitive states.

BACKGROUND

Brainwaves are produced by synchronized electrical pulses from masses of neurons in the brain communicating with each other. Furthermore, brainwaves alter in response to changes in environmental stimuli, including sound and music.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

The electrical activity of the brain has a cyclic, wave-like characteristic and is commonly known as a brainwave pattern. The electrical activity can be detected using sensitive medical equipment such as devices that employ electroencephalography (EEG). Brainwaves have various component frequencies like delta, theta, alpha, beta, and gamma.

Different ones of the brainwave frequencies are the dominant frequency in a brainwave pattern during different cognitive and/or emotional states. For example, delta frequencies (between about 0.1 Hz to above 3.9 Hz) are dominant during a deep, trance-like, nonphysical state in which the person has access to the unconscious and collective unconscious mind and experiences a loss of body awareness. Delta frequencies are prominent during dreamless sleep and when human growth hormone is released. Theta frequencies (between about 4 Hz to about 7.9 Hz) are dominate during dreaming sleep, i.e., rapid eye movement (REM) sleep. In this state, the person experiences hypnagogic imagery, trance, deep meditation, and access to the unconscious mind. During times with dominant theta frequency activity, there is an increased production of catecholamines, which are vital for learning and memory. There is also increased creativity, integrative and emotional experiences, potential changes in behavior, and increased retention of learned material. Alpha frequencies (between about 8 Hz and about 13.9 Hz) are dominant during states of relaxation, surperlearning, relaxed focus, and light trance. During times of dominant alpha frequency activity there is increased serotonin production, and the person experiences the beginning of access to the unconscious mind. Alpha frequencies are prominent during pre-sleep, pre-waking drowsiness, and meditation. Beta frequencies (between about 14 HZ to about 30 Hz) are dominant during states of concentration, arousal, alertness, and cognition. The higher level beta frequencies are associated with anxiety, disease, feelings of separation, and the fight or flight response. Gamma frequencies (over about 30 Hz) are dominant during conscious attention.

A healthy brain keeps changing its cognitive state such as, for example, being active, stressed, drowsy, etc. A person may experience stress or other discomfort from being in the same state for an extended period of time. For example, it is stressful to be in a fixed state of alertness for long duration. The examples disclosed herein facilitate the transition from one cognitive state to another.

In addition, brainwaves synchronize with or entrain to that of an external acoustic or photic stimulus, with accompanying alterations in cognitive and emotional state. This process is called neuronal entrainment or brainwave entrainment. Thus, exposure to specific frequencies can cause the brainwaves of a person to sync with those frequencies, which has the physical effect of altering the cognitive state of the person to the cognitive states associated with the respective frequencies.

The examples disclosed herein use binaural beats to effectively entrain and synchronize the brainwaves of a person to enhance a specific brainwave pattern. A binaural beat is an auditory illusion perceived when two different pure-tone sine waves, both with frequencies lower than 1500 Hz, with less than a 40 Hz difference between them, are presented to a listener dichotically (one through each ear). Thus, exposing a person to binaural beats to change the person's brainwave pattern to cause a dominant alpha, beta, gamma, etc. brainwave pattern will cause the person to rapidly enter the cognitive state associated with the dominant frequency including, for example, states of relaxation, focus, high-energy, or meditation. However, as disclosed below, the frequency of the binaural beat needed to entrain a user to a particular cognitive state varies from user to user.

The examples disclosed herein assist users to transition from one cognitive state to another. Specifically, the examples disclosed herein use EEG signals to monitor the brain signals of the user. For example, a brain signal analyzer can be used that monitors the brain signals, detects the dominant frequencies (e.g., alpha, beta, gamma, theta, delta) in these signals, and ascertains the current cognitive state of the brain.

Machine learning based processes and algorithms are used to control the cognitive state of the user by using the brainwave entrainment concept and binaural beats specific to the user's experience. Specifically, the brainwave entrainment changes the user's cognitive state or mood to a user-defined state or any desired state (e.g. alertness, relaxation, induced sleep) by dynamically configuring the frequency of the binaural beats based on the desired user-mode so the brain entrains to the desired frequency. These examples further consider the user's history of brainwave entrainment (e.g., what binaural beats have worked in the past). Thus, these examples continuously learn about the user's reaction to the rendered binaural beats. In such examples, the audio content will be automatically altered by reducing or increasing the frequency difference being rendered to both of the ears to best suit the particular user's desired cognitive state. In addition, the examples disclosed herein continuously monitor the EEG signals to determine if the user is responding to the audio being rendered. Adjustments can be made to dynamically alter the binaural beats in response to the user's reaction, which provides a tailor-made response. Also, in some examples, there are alterations to the visual content to facilitate the transition from one cognitive state to another cognitive state.

The examples disclosed herein have significance in a virtual reality use-case where the user gets more mentally involved and experiences higher stress due to the immersive nature of the content. As disclosed above, to relax the user and bring the user to a better cognitive state, an example brain entrainment technique is applied using binaural beats, which will help user alleviate stress and enter a more desirable cognitive state. Additional changes to the visual content are also utilized, including, for example, presenting virtual reality video content such as space travel or sea waves along with the binaural beats to facilitate and accelerate the cooling down. This enables the player to return to an optimal (e.g., calmer) state quickly.

Figure 1:
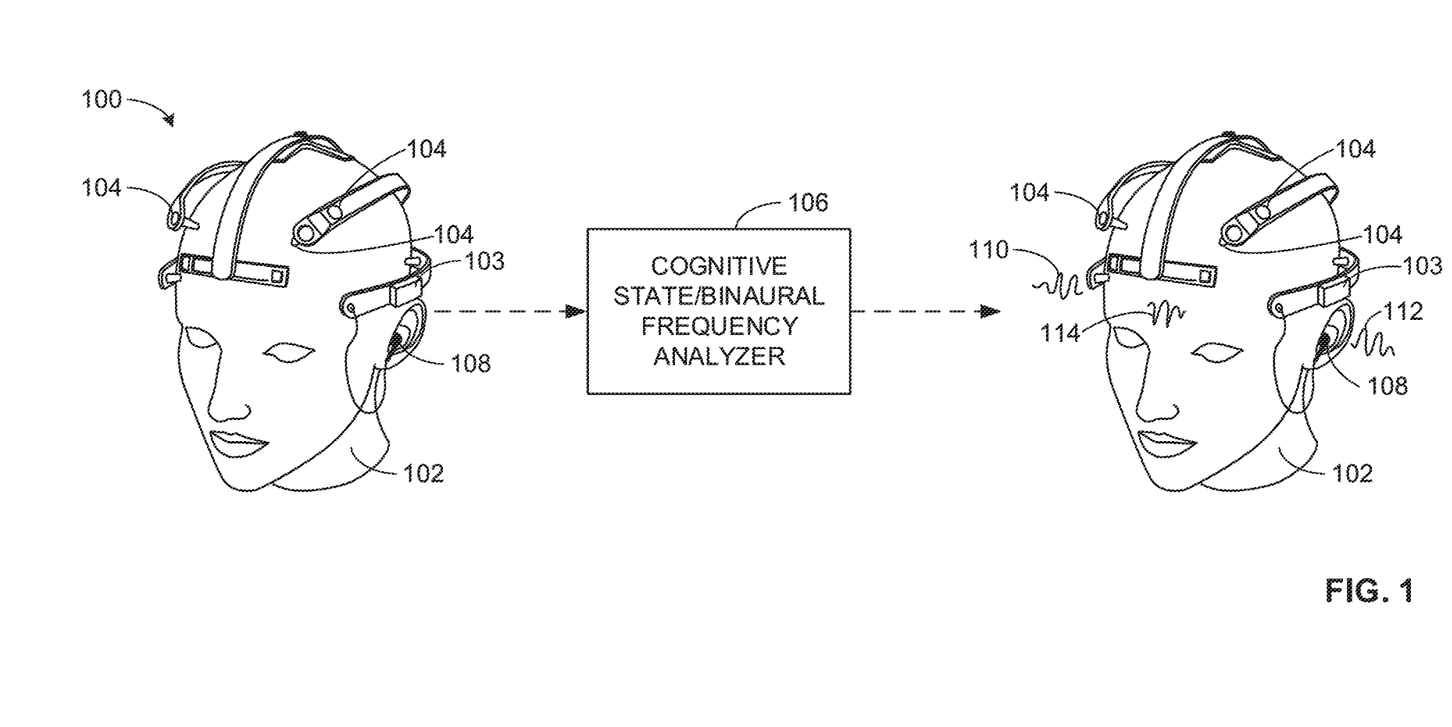
FIG. 1 is a schematic illustration of an example system for configuring a cognitive state in accordance with the teachings of this disclosure.

FIG. 1 is a schematic illustration of an example system 100 for configuring a cognitive state of a user 102. In the example system 100, there are one or more example sensors 104 that gather data from the user 102. In this example, the sensors 104 are electrodes carried by a headset 103 and placed in contact with the user's head. The sensors 104 gather EEG data. The EEG is analyzed in an example cognitive state/binaural frequency analyzer 106, which is disclosed in greater detail below. The cognitive state/binaural frequency analyzer 106 determines both the cognitive state of the user 102 and the binaural beats to present to the user 102 to change the cognitive state to a desired cognitive state. The example system 100 include an example output 108, which in this example, includes speakers in headphones, to present the binaural beats to the user 102. A first waveform 110 having a first frequency is presented to one ear, and dichotically a second waveform 112 having a second frequency is presented at the other ear simultaneously. The difference between the two frequencies is perceived by the brain as the binaural beat 114.

Figure 2:
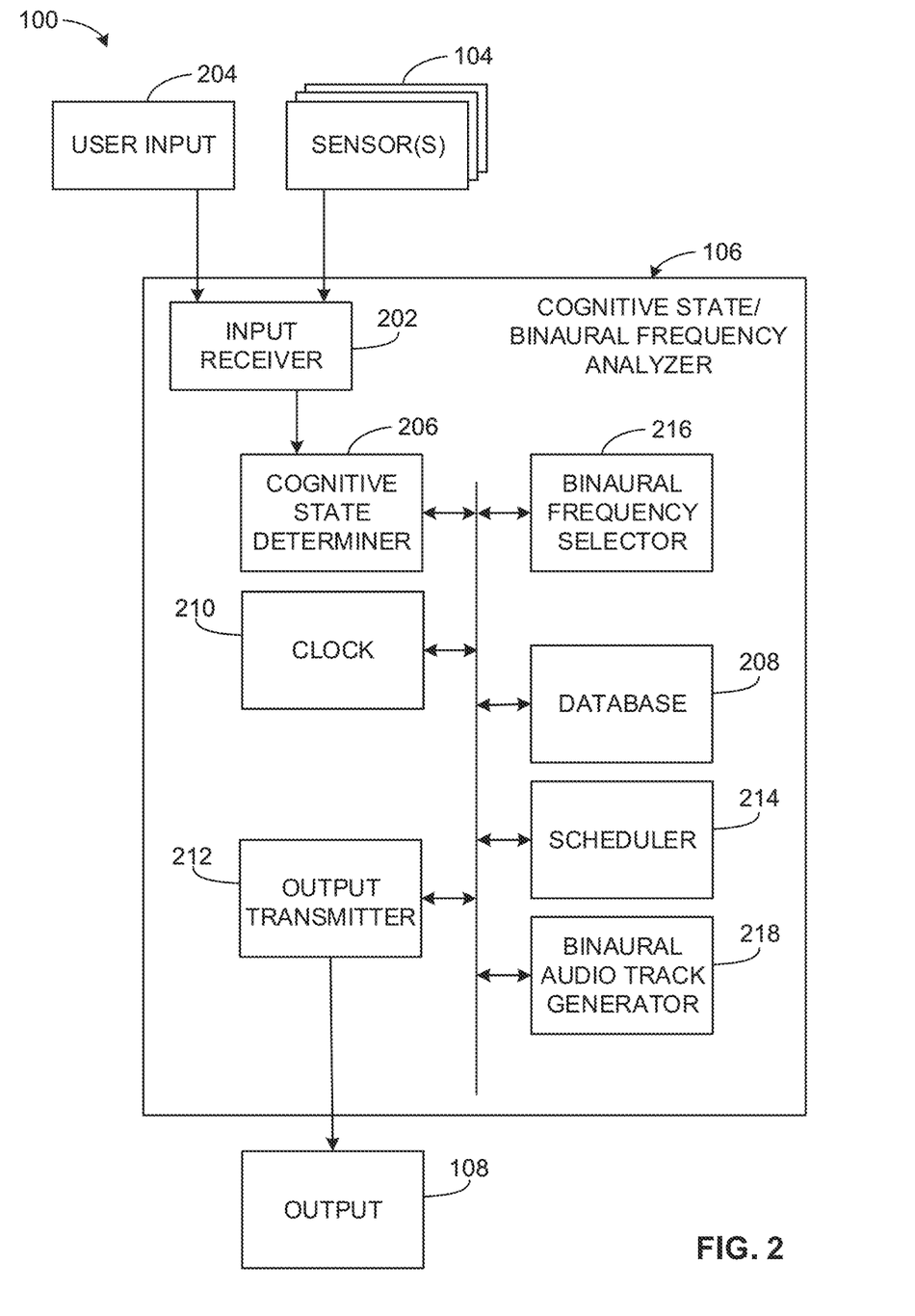
FIG. 2 is a block diagram of the example system of FIG. 1.

FIG. 2 is a block diagram of the example system 100 of FIG. 1 in which the sensors 104 are coupled to the cognitive state/binaural frequency analyzer 106 via an example input receiver 202. In this example, the input receiver 202 includes any suitable wired or wireless means for receiving data for communication to the cognitive state/binaural frequency analyzer 106. For example, the sensors 104 can be one or more electrodes that gather EEG data from the user's head. The sensors 104 can transmit raw EEG or processed EEG data (e.g., data that has been filtered, amplified, and/or digitized) to the input receiver 202 of the cognitive state/binaural frequency analyzer 106 via wired connections along a printed circuit board (PCB) or wireless connections using, for example, radio waves. As disclosed above, the sensors 104 can be mounted to the headset 103. The sensors 104 continuously monitor the EEG data from the user 102 for analysis by the cognitive state/binaural frequency analyzer 106.

The example system 100 also includes an example user input 204. The user input 204 can be used by the user 102 whose EEG data is being gathered, a medical professional, or other caretaker to provide input to the cognitive state/binaural frequency analyzer 106. For example, the user 102 can input instructions via the user input 204 to bring the user 102 to a second cognitive state upon detection of a first cognitive state. For example, the user 102 can instruct the cognitive state/binaural frequency analyzer 106 to bring the user 102 to a calmer cognitive state after the user 102 has reached a state of high activity indicative of anxiety. The example user interface 204 can be any wired or wireless input technology including, for example, a keyboard, a key pad, a mouse, a touch screen, a radio transmitter, a joystick, a scanner, a camera, a light pen, a pointing device, or any other suitable device for communicating information to the cognitive state/binaural frequency analyzer 106.

The example system also includes an example cognitive state determiner 206 that determines the cognitive state of the user 102 from the EEG data gathered by the sensors 104. In some examples, the cognitive state determiner 206 analyzes the raw EEG data. In other examples, the cognitive state determiner 206 analyzes pre-processed data received by the input receiver 202 such as, for example, raw data that has been processed by the sensors 104, as disclosed above. The EEG processing completed by the cognitive state determiner 206 or at the sensors 104 includes digitizing the EEG data for analysis. Noise components from the EEG data are removed to exclude data associated with, for example, a user's heartbeat and data from a power source. The signals are then transformed using wavelet transforms to separate frequency bands. The cognitive state determiner 206 also runs dimensionality reduction algorithms like Principal Component Analysis or Independent Component Analysis, etc. along with classification algorithms such as, for example, support vector machine learning algorithms or decision trees to determine the dominant frequency bands. The dominant frequency bands indicate the current cognitive state.

In addition, the cognitive state determiner 206 trains the classification algorithm based on known mapping of the different frequencies to the different cognitive states. In addition, training of the classification algorithm will be continuously and automatically updated with the user's data to refine the frequency/cognitive state mapping for the particular user. An example mapping is shown in Table 1.

TABLE 1

| Frequency | Cognitive State |
| --- | --- |
| Beta Waves: 15-30 Hz | Normal waking state: alert, eyes open and/or anxious. |
| Alpha Waves: 7-14 Hz | Relaxation: eyes closed, no mental exertion. |
| Theta Waves: 4-7 Hz | Deep relaxation: light sleep, meditation, and creative states (also normally in young children). |
| Delta Waves: up to 4 Hz | Deep sleep: slow eave sleep (non-REM), highest in amplitude and slowest waves. |

The known mapping and the user data may be stored in an example database 208. Thus, in these example, the cognitive state determiner 206 determines the current cognitive state of the user 102 with algorithms that are enhanced with machine-learning routines so that the user's own experience, disposition, and physiological idiosyncrasies are used to select the binaural beats and/or dynamically modify the binaural beats to entrain the user to a desired cognitive state.

Figure 3:
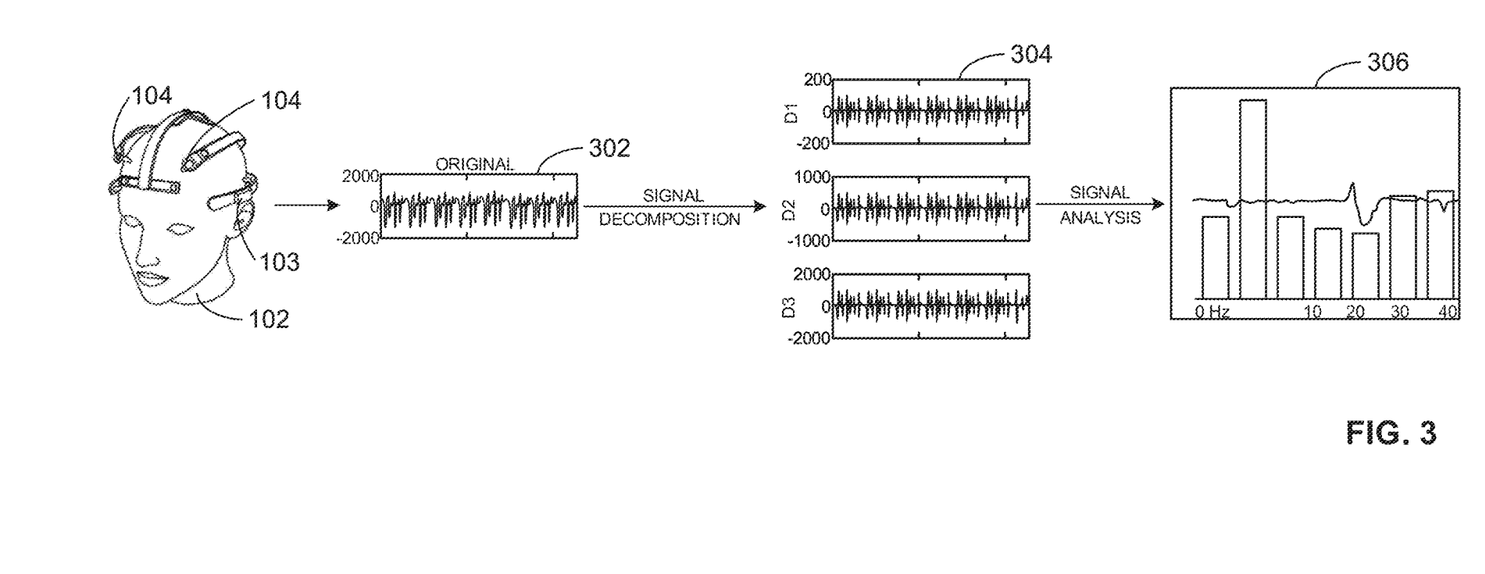
FIG. 3 is a diagram that shows the transformation of raw EEG data into a histogram indicative of dominant brainwave frequencies.

FIG. 3 is a diagram that shows the transformation of raw EEG data 302 via a signal decomposition 304 into a histogram 306. In this example, the histogram 306 shows that the dominant frequency is in the sub 4 Hz range. This indicates that the user, in this example, is in the cognitive state corresponding to the delta waves (i.e., the user is sleeping).

The cognitive state/binaural frequency analyzer 106 also includes an example clock 210 (FIG. 2). The clock 210 is used to keep track of the duration for which the user 102 is in a particular cognitive state. In some examples, using the data from the clock 210, the cognitive state/binaural frequency analyzer 106 determines that the user 102 has been in a specific cognitive state long enough and that it is apt for the user 102 to switch to a lower cognitive state. In such examples, the cognitive state/binaural frequency analyzer 106 can notify the user 102 to switch to a different cognitive state by, for example, sending a message through an example output transmitter 212 to the output 108. The message can be, for example, an audio and/or visual message. In other examples, the message could be tactile such as, for example, a vibration.

In some example, the cognitive state/binaural frequency analyzer 106 will ask the user 102 what cognitive state the user 102 would desire to switch to, to which the user 102 can respond via the user input 204. In other examples, the cognitive state/binaural frequency analyzer 106 automatically determines the cognitive state the user 102 needs to or should be in based on the prior cognitive state and/or the duration of time in the prior cognitive state. For example, during an intense virtual reality game play, the cognitive state determiner 206 determines that the user 102 has been in the cognitive state corresponding to that of beta waves (high alertness) for a long time leading to stress. The cognitive state/binaural frequency analyzer 106 will then notify the user 102 to switch to a lower cognitive state like alpha and/or theta to cool down the user 102. The game play can be paused during the duration of cooling down and may be resumed later. In some examples, the cognitive state/binaural frequency analyzer 106 automatically pauses and resumes the game based on the cognitive state.

In addition, the cognitive state/binaural frequency analyzer 106 includes an example scheduler 214, which may contain a user's schedule of activities or engagements. In this example, the cognitive state determiner 206 implicitly determines the desired cognitive state for the user 102 based on the user's schedule. For example, before the user 102 is scheduled to engage in a meeting or training session in virtual reality or reality, the cognitive state/binaural frequency analyzer 106 can access this information from the scheduler 214 and cognitive state determiner 206 can determine that user 102 needs to be brought from a state of relaxation to a state of high level of concentration.

The cognitive state/binaural frequency analyzer 106 also includes an example binaural frequency selector 216. The binaural frequency selector 216 determines the binaural frequencies to use to entrain the user 102 to the desired cognitive state. For example, the binaural frequency selector 216 uses the desired cognitive state as an input in a regression algorithm. The binaural frequency selector 216 further uses input from the cognitive state determiner 206 that maps the user's cognitive state with different frequencies to arrive at the frequency of the binaural beat to be generated to reach the desired cognitive state.

The example system 100 also includes an example binaural audio track generator 218. The binaural audio track generator 218 uses the frequency of the binaural beat selected by the binaural frequency selector 216 to generate the frequencies of the audio that is to be delivered to the user 102 via, for example, the output 108. In the example of FIG. 1, the binaural frequency audio track is delivered using a stereo headphone 108.

For example, as shown in FIG. 1, the first binaural frequency 110, which in this example is a sinusoidal audio wave of 124 Hz, is delivered to one of the ears of the user 102. At the same time, the second binaural frequency 112, which in this example is a sinusoidal wave of a 114 Hz, is delivered to the other ear of the user 102. The difference between the two binaural frequencies is the binaural beat 114, which in this example is 10 Hz. The user's brain perceives the binaural beat frequency of 10 Hz. That is, while 124 Hz is played in one ear and 114 Hz is played in another ear, the user effectively hears 10 Hz. In this example, 10 Hz, which falls in the alpha wave band, corresponds to relaxation. Humans rarely perceive frequencies below 20 Hz, so this process can be used to create the audio illusion of a person effectively hearing, due to the brain's perception, 10 Hz.

In another example, if the binaural frequency selector 216 determines that a binaural beat of 20 Hz as a single mono tone sinusoidal music track is to be played to deliver the user 102 to a desired cognitive state. To generate a 20 Hz binaural beat as a difference between two frequencies, the binaural frequency selector 216 selects a 100 Hz mono tune music and then determines that the frequency of one channel to one of the user's ears is up-leveled to 110 Hz while the frequency of the other channel to the other ear is down-leveled to 90 Hz. The difference in the two frequencies in the two channels is what the brain would perceive as 20 Hz binaural beats.

As the binaural beats are being delivered to the user 102, the EEG sensors 104 continue to capture the user's EEG data. This provides a feedback loop to verify that the brain is entraining to the desired state. The cognitive state/binaural frequency analyzer 106 analyses the user's current cognitive state and the response to the binaural audio rendered. For example, if the binaural beats frequency being rendered is 20 Hz, then the cognitive state/binaural frequency analyzer 106 analyses if the user 102 is getting entrained to the cognitive state corresponding to this frequency or not. In this example, the 20 Hz frequency corresponds to a normal waking state, which would be used to warm up the user 102 such as, for example, before a training session. If the cognitive state/binaural frequency analyzer 106 determines that the user 102 is not entraining to the desired cognitive state based on the EEG data gathered from the sensors 104 and the analysis of the cognitive state determiner 206, the cognitive state/binaural frequency analyzer 106 can operate the binaural frequency selector 216 to adjust the binaural frequencies to be delivered to the user 102 in an effort to properly entrain the user 102 as desired. Thus, the user's own response is factored into the selection of binaural beats used to entrain the user to the desired cognitive state.

When the user 102 is entrained as desired, the mapping of frequencies to cognitive states can be updated with user-specific information. Thus, the cognitive state/binaural frequency analyzer 106 adopts machine learning algorithms that determine the current cognitive state and the binaural frequency to be rendered to bring the user 102 to the required cognitive state. This frequency varies from person to person, and the machine learning process of determining the binaural frequency provides a customized frequency best suited for the user 102 to entrain to a particular cognitive state. The closed-loop model of this machine learning is continuously trained with the user's response to the selected binaural frequency to increase the accuracy of the selected binaural frequencies for particular desired cognitive states.

Once it is determined that the user 102 has entrained to the desired cognitive state, the cognitive state/binaural frequency analyzer 106 can take subsequent action including, for example, entraining the user 102 to another desired state and/or enabling the user 102 to proceed with an activity.

For example, in the virtual reality gaming environment, cognitive state/binaural frequency analyzer 106 determines that the user 102 has been in stress for a prolonged duration by analyzing the EEG data captured via the sensors 104. The cognitive state/binaural frequency analyzer 106 interrupts the user's game play by allowing the user 102 to pause the game or pausing the game for the user 102. The cognitive state/binaural frequency analyzer 106 provides the user 102 with a few options to cool down including, for example, via relaxation or sleep. To bring the user 102 to the desired cognitive state the cognitive state/binaural frequency analyzer 106 presents the selected binaural beats coupled with selected video including, for example, waves crashing or space travel for an immersive virtual reality experience to facilitate the cool down. Once the cognitive state/binaural frequency analyzer 106 determines that the user 102 is sufficiently cooled down based on, for example, EEG data indicative of cognitive state and a desired time period, the cognitive state/binaural frequency analyzer 106 can then bring the user 102 to a higher level of attention/concentration if desired by generating a binaural beat in the frequency band of beta, where the user 102 will resume the game play.

In other examples, the cognitive state/binaural frequency analyzer 106 can be trained for use in prepping up the user 102 before work or school, cooling down the user 102 for relaxation after work, improving sleep at night, improving mental ailments such as reducing anxiety, among other uses.

While an example manner of implementing the system 100 of FIG. 1 is illustrated in FIG. 2, one or more of the elements, processes and/or devices illustrated in FIG. 2 may be combined, divided, re-arranged, omitted, eliminated and/or implemented in any other way. Further, the example input receiver 202, the example user input 204, the example cognitive state determiner 206, the example database 208, the example clock 210, the example output transmitter 212, the example scheduler 214, the example binaural frequency selector 216, the example binaural audio track generator 218, and/or, more generally, the example the cognitive state/binaural frequency analyzer 106 of FIG. 2 may be implemented by hardware, software, firmware and/or any combination of hardware, software and/or firmware. Thus, for example, any of the example input receiver 202, the example user input 204, the example cognitive state determiner 206, the example database 208, the example clock 210, the example output transmitter 212, the example scheduler 214, the example binaural frequency selector 216, the example binaural audio track generator 218, and/or, more generally, the example the cognitive state/binaural frequency analyzer 106 of FIG. 2 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example input receiver 202, the example user input 204, the example cognitive state determiner 206, the example database 208, the example clock 210, the example output transmitter 212, the example scheduler 214, the example binaural frequency selector 216, the example binaural audio track generator 218, and/or, more generally, the example the cognitive state/binaural frequency analyzer 106 of FIG. 2 is/are hereby expressly defined to include a non-transitory computer readable storage device or storage disk such as a memory, a digital versatile disk (DVD), a compact disk (CD), a Blu-ray disk, etc. including the software and/or firmware. Further still, the example system 100 of FIG. 1 may include one or more elements, processes and/or devices in addition to, or instead of, those illustrated in FIG. 2, and/or may include more than one of any or all of the illustrated elements, processes and devices.

Figure 4:
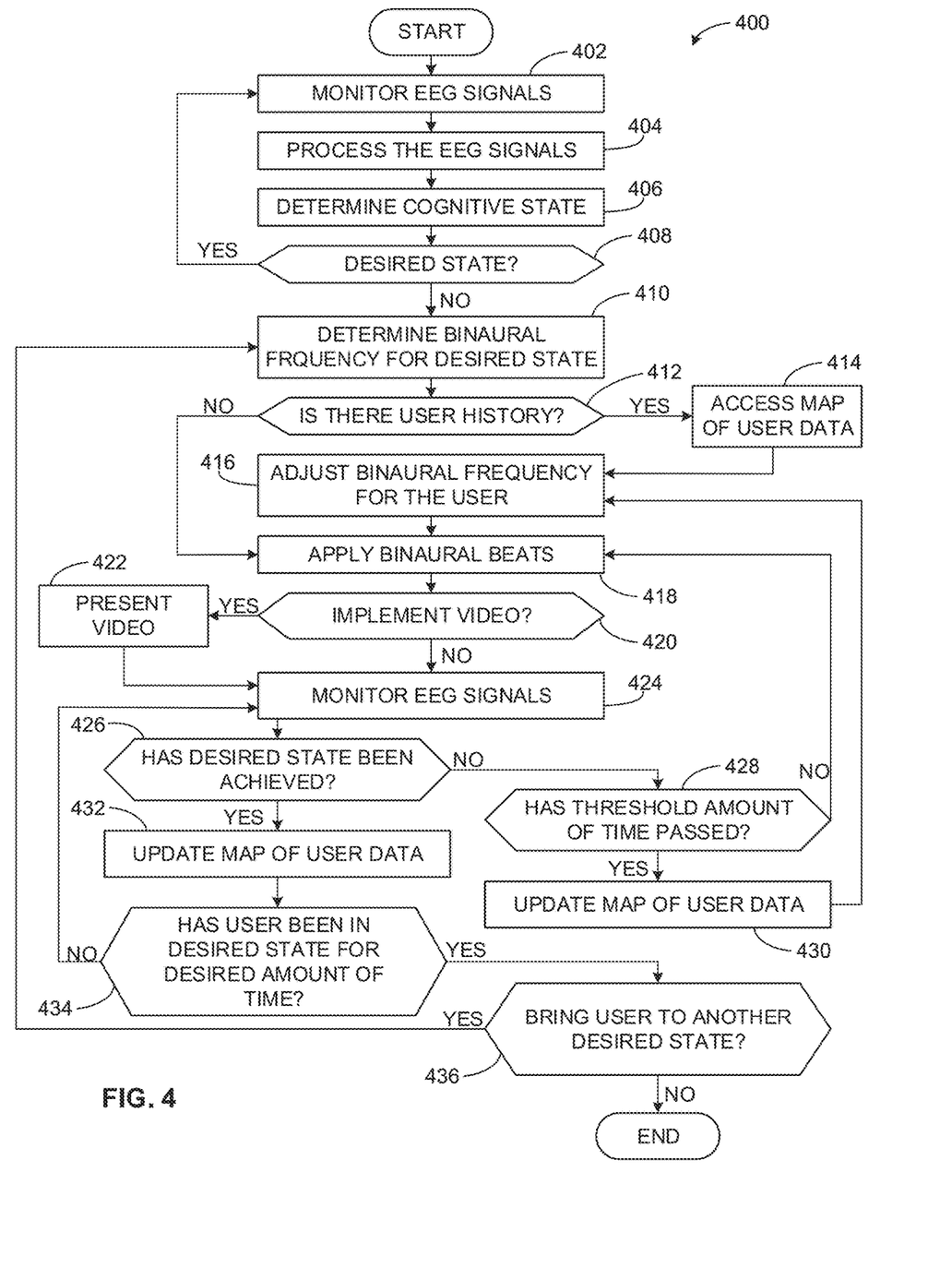
FIG. 4 is a flow chart representative of example machine readable instructions that may be executed to implement the example system of FIGS. 1 and 2.

A flowchart representative of example machine readable instructions for implementing the system 100 of FIGS. 1 and 2 is shown in FIG. 4. In this example, the machine readable instructions comprise a process or program 400 for execution by a processor such as the processor 512 shown in the example processor platform 500 discussed below in connection with FIG. 5. The program 400 may be embodied in software stored on a non-transitory computer readable storage medium such as a CD-ROM, a floppy disk, a hard drive, a digital versatile disk (DVD), a Blu-ray disk, or a memory associated with the processor 512, but the entire program 400 and/or parts thereof could alternatively be executed by a device other than the processor 512 and/or embodied in firmware or dedicated hardware. Further, although the example program 400 is described with reference to the flowchart illustrated in FIG. 4, many other methods of implementing the example drone 100 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example program 400 of FIG. 4 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

The program 400 of FIG. 4 begins with monitoring data from a user including monitoring of EEG signals (block 402). For example, the sensors 104 including electrodes mounted to the headset 103 are used to gather EEG data from a user's head. The example program 400 also includes processing the EEG signals (block 404). In some examples, the EEG signals are pre-processed at the electrodes including amplification and filtering for noise reduction. In some examples, the raw EEG data and/or pre-processed EEG data is analyzed in the cognitive state/binaural frequency analyzer 106. The example program 400 determines, based on the EEG data, the cognitive state of the user (block 406). For example, the cognitive state determiner 206 analyzes the EEG data and determines the user's cognitive state based on the dominant frequency band in the EEG data, as disclosed above.

The example program 400 also determines whether or not the user is in a desired cognitive state (block 408). For example, the cognitive state/binaural frequency analyzer 106 uses data from the user input 204, the cognitive state determiner 206, the database 208, the clock 210, and/or the scheduler 214 to determine if the current user cognitive state is the desired cognitive state. If the current cognitive state is the desired cognitive state, the example program 400 returns to continue monitoring the EEG signals (block 402).

If the current cognitive state is not the desired cognitive state, the example program 400 determines binaural frequencies to create a binaural beat for presentation to the user to entrain the user's brain to the desired state (block 410). For example, the binaural frequency selector 216 selects the frequencies to present to the user via, for example, the output 108. As disclosed above, if the user is in a high state of attention and the desired state is a calmer state, the binaural frequency selector 216 may select binaural frequencies of 114 Hz and 124 Hz to present via headphones to respective ones of the user's ears. The difference between these two frequencies is the binaural beat perceived by the user's brain. In this example, the binaural beat is 10 Hz, which is an alpha wave associated with relaxation. In some examples, the database 208 includes a mapping of brain wave frequencies and associated cognitive states to facilitate operation of the binaural frequency selector 216.

In some examples, a user's own historical data is used to influence the selection of binaural frequencies. In such examples, the example program 400 determines if there is data available related to a user's history (block 412). If there is user historical data, the example program 400 accesses a map of user data (block 414). In some examples, the database 208 includes the mapping, as disclosed above, which includes data related to what frequencies has been successful or unsuccessful in entraining the user to different cognitive states. The historical user data may be used to adjust the selected binaural frequencies (block 416).

With the selected binaural frequencies (block 410) or the adjusted binaural frequencies (block 416), the example program 400 continues and presents the frequencies to the user to apply the binaural beat as disclosed above (block 418). The example program 400 also determines if video should be presented to supplement the binaural frequencies (block 420). For example, the cognitive state/binaural frequency analyzer 106 may determine to present video such as crashing ocean waves to a user in a virtual reality environment to facilitate the transition from a cognitive state of heightened attention to a calmer cognitive state. In such example, the example program 400 includes presenting the video (block 420). The video can be presented, for example, via the output 108, which may include any suitable display device. If the example program 400 determines not to implement video (block 420) or once the video is presented (bloc 422), the example program 400 continues with monitoring of the EEG signals from the user (block 424). For example, the sensors 104 continue to gather EEG data and transmit the data to the cognitive state/binaural frequency analyzer 106.

Based on the gathered EEG data, the example program 400 determines if the user has achieved the desired cognitive state (block 426). For example, the cognitive state determiner 206 analyzes the user's EEG data during and/or after application of the binaural beats and reassess the user's current state. If the current state does not match the desired cognitive state, the example program 400 determines if a threshold amount of time has passed (block 428). For example, the clock 210 gathers time data, which can be used by the cognitive state/binaural frequency analyzer 106 to assess whether or not the binaural beats have been applied to the user for a sufficient or threshold amount of time. People may not instantaneously transition from one cognitive state to another. A period of time is needed to entrain the brain after the presentation of the binaural beats. The threshold amount of time may be based on general population data, specific demographic information including, for example age, and/or user specific data based on historical attempts of brain entrainment for the specific user.

If a threshold amount of time has not passed, the example program 40 continues with the application of the binaural beats (block 418). If a threshold amount of time has passed and the user is not in the desired cognitive state, the example program 400 updates the map of the user's historical data to reflect that the threshold amount of time of the applied binaural beat was not successful for entraining the user's brain to the desired cognitive state (block 430). For example, the cognitive state/binaural frequency selector 106 can update the database 208 to reflect that the combination of binaural beats and time was insufficient for a successful cognitive state transition for the particular user, which is data that may be used in the future to select different binaural beats and/or a different threshold amount of time for presenting the binaural beats to the user for a similar desired cognitive state transition. After an unsuccessful transition to a desired cognitive state, the example program 400 returns to adjust the binaural frequency for the user (block 416).

If the example program 400 determines that the desired cognitive state has been achieved (block 426), then the program 400 updates the map of user data to reflect the success (block 432). The example program 400 also determines if the user has been in the desired cognitive state for a desired amount of time (block 434). For example, the cognitive state/binaural frequency analyzer 106 uses data from the sensors 104, cognitive state determiner 206, clock 210, and scheduler 214 to assess if the user has been in a desired state for a desired amount of time. In the virtual reality gaming environment example, the cognitive state/binaural frequency analyzer 106 determines if the user has been cooled down long enough to resume play.

If the user has not been in the desired cognitive state for the desired amount of time, the example program 400 continues to monitor the EEG signals (block 424). The example program 400 further continues to monitor that the user is in the desired cognitive state (block 426). If the example program 400 determines that user has been in the desired cognitive state for the desired amount of time (block 434), the example program 400 determines if the user should be brought to another desired cognitive state (block 436). For example, the cognitive state/binaural frequency analyzer 106 uses data from the sensors 104, user input 204, cognitive state determiner 206, clock 210, and scheduler 214 to assess if the user should be brought to another desired cognitive state. In the virtual reality gaming environment example, the cognitive state/binaural frequency analyzer 106 determines whether or not a user needs to be warmed up to resume play.

If the example program determines that the user is to be brought to another desired cognitive state, the example program 400 returns to select a binaural frequency to present to the user to entrain the user's brain to the next desired cognitive state (block 410). If the example program determines that the user is not to be brought to another desired cognitive state (block 436), the example program 400 ends.

Figure 5:
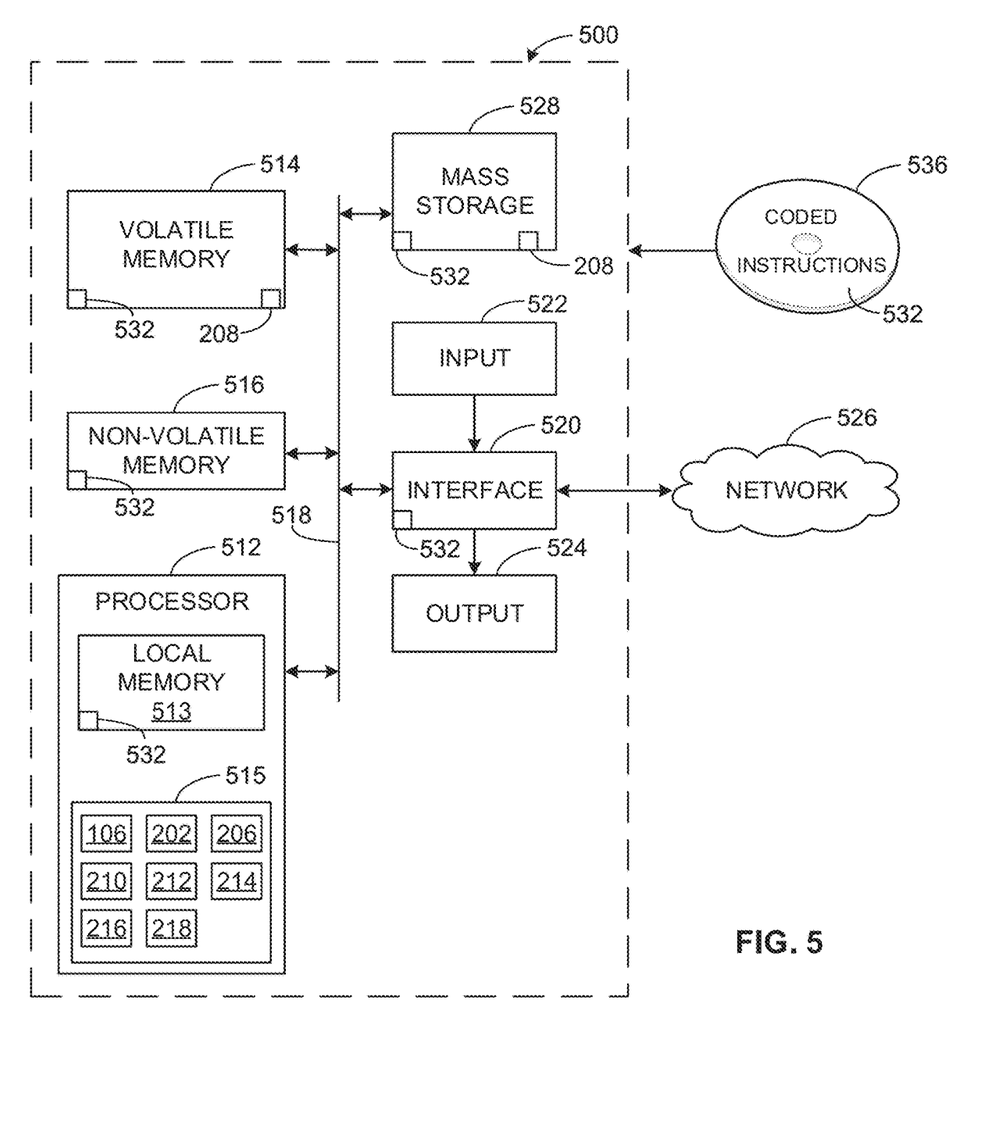
FIG. 5 is a block diagram of an example processor platform structured to execute the example machine readable instructions of FIG. 4 to implement the example system of FIGS. 1 and 2.

FIG. 5 is a block diagram of an example processor platform 500 capable of executing the instructions of FIG. 4 to implement the apparatus of FIGS. 1 and 2. The processor platform 500 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 500 of the illustrated example includes a processor 512. The processor 512 of the illustrated example is hardware. For example, the processor 512 can be implemented by one or more integrated circuits, logic circuits, microprocessors or controllers from any desired family or manufacturer. The hardware processor may be a semiconductor based (e.g., silicon based) device. In this example, the processor implements the example input receiver 202, the example cognitive state determiner 206, the example clock 210, the example output transmitter 212, the example scheduler 214, the example binaural frequency selector 216, the example binaural audio track generator 218, and/or the example the cognitive state/binaural frequency analyzer 106 of FIG. 2.

The processor 512 of the illustrated example includes a local memory 513 (e.g., a cache). The processor 512 of the illustrated example is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 may be implemented by flash memory and/or any other desired type of memory device. Access to the main memory 514, 516 is controlled by a memory controller.

The processor platform 500 of the illustrated example also includes an interface circuit 520. The interface circuit 520 may be implemented by any type of interface standard, such as an Ethernet interface, a universal serial bus (USB), and/or a PCI express interface.

In the illustrated example, one or more input devices 522 are connected to the interface circuit 520. The input device(s) 522 permit(s) a user to enter data and/or commands into the processor 512. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 524 are also connected to the interface circuit 520 of the illustrated example. The output devices 524 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 520 of the illustrated example, thus, typically includes a graphics driver card, a graphics driver chip and/or a graphics driver processor.

The interface circuit 520 of the illustrated example also includes a communication device such as a transmitter, a receiver, a transceiver, a modem and/or network interface card to facilitate exchange of data with external machines (e.g., computing devices of any kind) via a network 526 (e.g., an Ethernet connection, a digital subscriber line (DSL), a telephone line, coaxial cable, a cellular telephone system, etc.).

The processor platform 500 of the illustrated example also includes one or more mass storage devices 528 for storing software and/or data. Examples of such mass storage devices 528 include floppy disk drives, hard drive disks, compact disk drives, Blu-ray disk drives, RAID systems, and digital versatile disk (DVD) drives.

The coded instructions 532 of FIG. 4 may be stored in the mass storage device 528, in the volatile memory 514, in the non-volatile memory 516, and/or on a removable tangible computer readable storage medium such as a CD or DVD.

From the foregoing, it will be appreciated that example methods, apparatus and articles of manufacture have been disclosed that binaural beats to transition a user from one cognitive state to another cognitive state. Further, the examples disclosed here use the user's own history of responses to binaural beats in the selection of binaural beats so that the brain entrainment from one cognitive state to another cognitive state is a tailor-made process that enhances user experience and increases the likelihood of success or the rate of success of the binaural beats in effecting the cognitive state transition.

As mentioned above, this solution has varied applications in virtual reality gaming. A user can be quickly cooled down after an intense game play or after detecting abnormal brain activity via EEG sensors. The selected binaural beat frequency and, in some examples, an accompanying video, is used to entrain the user's cognitive state to a calmer state.

The systems, methods, and apparatus disclosed herein also can be used to facilitate, virtual reality based learning, tutoring, and meetings by warming a user up to a more attentive cognitive state in advance of the activity.

Other benefits of these disclosed examples include improving sleep at night, improving mental ailments such as reducing anxiety, among other uses.

These example systems, methods, and apparatus may be implemented on a user-by user basis for individual applications and also are scalable to all users. Further examples and combinations thereof include the following.

Example 1 is a system to change a cognitive state of a user. The example system includes a sensor to gather first electroencephalographic data from the user. The example system also includes an analyzer to determine a first cognitive state of the user based on the first electroencephalographic data, and to determine a first binaural beat to present to the user based on the first cognitive state and a second cognitive state. In addition, the example system includes an output to present the first binaural beat to the user. In the example system, the sensor is to gather second electroencephalographic data from the user exposed to the first binaural beat, and the analyzer is to determine a first effectiveness of the first binaural beat to place the user in the second cognitive state and to determine a second binaural beat to present to the user based on the first cognitive state, the second cognitive state, and the second electroencephalographic data. In the example system, the output is to present the second binaural beat to the user. The analyzer in the example system is to determine a second effectiveness of the second binaural beat to place the user in the second cognitive state, to perform a comparison of the first effectiveness and the second effectiveness, and to select one of the first binaural beat or the second binaural beat for future presentation to the user to change the cognitive state of the user to the second cognitive state based on the comparison.

Example 2 includes the system of Example 1, wherein the output includes a first speaker to present a first frequency to a first ear of the user and a second speaker to present a second frequency to a second ear of the user, the first binaural beat being a difference between the first frequency and the second frequency.

Example 3 includes the system of Example 2, wherein the first speaker is to present a third frequency to the first ear of the user, the second binaural beat being a difference between the third frequency and the second frequency.

Example 4 includes the system of Example 2, wherein the first speaker is to present a third frequency to the first ear of the user and the second speaker is to present a fourth frequency to the second ear of the user, the second binaural beat being a difference between the third frequency and the fourth frequency.

Example 5 includes the system of any of Examples 1-4, wherein the output includes a display to present a video concurrently with at least one of the first binaural beat or the second binaural beat.

Example 6 includes the system of Example 1, wherein the analyzer is to cause the output to automatically present the first binaural beat when the first cognitive state is determined.

Example 7 includes the system of Example 1, wherein the analyzer is to cause the output to automatically present a selected one of the first binaural beat or the second binaural beat based on a subsequent detection of the first cognitive state.

Example 8 includes the system of Examples 6 or 7, wherein the analyzer is to pause a game to change the cognitive state of the user.

Example 9 includes the system of any of Examples 1-4, 6, or 7, wherein the analyzer is to determine a third binaural beat to present to the user to change the cognitive state of the user to the first cognitive state or a third cognitive state after a period of time in the second cognitive state.

Example 10 is a system to change a cognitive state of a user in which the system includes means for gathering first electroencephalographic data from the user. The example system also includes means for analyzing data to determine a first cognitive state of the user based on the first electroencephalographic data, and to determine a first binaural beat to present to the user based on the first cognitive and a second cognitive state. In addition, the example system includes means for presenting the first binaural beat to the user. In the example system, the means for gathering is to gather second electroencephalographic data from the user exposed to the first binaural beat. In the example system, the means for analyzing is to determine a first effectiveness of the first binaural beat to place the user in the second cognitive state, and to determine a second binaural beat to present to the user based on the first cognitive state, the second cognitive state, and the second electroencephalographic data. In the example system, the means for presenting is to present the second binaural beat to the user. In addition, in the example system, the means for analyzing is to determine a second effectiveness of the second binaural beat to place the user in the second cognitive state, to perform a comparison of the first effectiveness and the second effectiveness, and to select one of the first binaural beat or the second binaural beat for future presentation to the user to change the user cognitive state to the second cognitive state based on the comparison.

Example 11 includes the system of Example 10, wherein the means for presenting includes a first speaker to present a first frequency to a first ear of the user and a second speaker to present a second frequency to a second ear of the user, the first binaural beat being a difference between the first frequency and the second frequency.

Example 12 includes the system of Example 11, wherein the first speaker is to present a third frequency to the first ear of the user, the second binaural beat being a difference between the third frequency and the second frequency.

Example 13 includes the system of Example 11, wherein the first speaker is to present a third frequency to the first ear of the user and the second speaker is to present a fourth frequency to the second ear of the user, the second binaural beat being a difference between the third frequency and the fourth frequency.

Example 14 includes the system of any of Examples 10-13, wherein the means for presenting includes a display to present a video concurrently with at least one of the first binaural beat or the second binaural beat.

Example 15 includes the system of Example 10, wherein the means for analyzing is to cause the means for presenting to automatically present the first binaural beat when the first cognitive state is determined.

Example 16 includes the system of Example 10, wherein the means for analyzing is to cause the means for presenting to automatically present a selected one of the first binaural beat or the second binaural beat based on a subsequent detection of the first cognitive state.

Example 17 includes the system of Example 15 or 16, wherein the means for analyzing is to pause a game to change the cognitive state of the user.

Example 18 includes the system of any of Examples 10-13, 15, or 16, wherein the means for analyzing is to determine a third binaural beat to present to the user to change the cognitive state of the user to the first cognitive state or a third cognitive state after a period of time in the second cognitive state.

Example 19 is a method to change a cognitive state of a user. The example method includes gathering first electroencephalographic data from the user, determining a first cognitive state of the user based on the first electroencephalographic data, determining a first binaural beat to present to the user based on the first cognitive and a second cognitive state, and presenting the first binaural beat to the user. The example method also includes gathering second electroencephalographic data from the user exposed to the first binaural beat, determining a first effectiveness of the first binaural beat to place the user in the second cognitive state, determining a second binaural beat to present to the user based on the first cognitive state, the second cognitive state, and the second electroencephalographic data, and presenting the second binaural beat to the user. In addition, the example method includes determining a second effectiveness of the second binaural beat to place the user in the second cognitive state, performing a comparison of the first effectiveness and the second effectiveness, and selecting one of the first binaural beat or the second binaural beat for future presentation to the user to change the user cognitive state to the second cognitive state based on the comparison.

Example 20 includes the method of Example 19, and also includes presenting a first frequency to a first ear of the user via a first speaker and presenting a second frequency to a second ear of the user via a second speaker, the first binaural beat being a difference between the first frequency and the second frequency.

Example 21 includes the method of Example 20, and also includes presenting a third frequency to the first ear of the user via the first speaker, the second binaural beat being a difference between the third frequency and the second frequency.

Example 22 includes the method of Example 20, and also includes presenting a third frequency to the first ear of the user via the first speaker and presenting a fourth frequency to the second ear of the user via the second speaker, the second binaural beat being a difference between the third frequency and the fourth frequency.

Example 23 includes the method of any of Examples 19-22, and also includes presenting a video concurrently with at least one of the first binaural beat or the second binaural beat.

Example 24 includes the method of Example 19, and also includes automatically presenting the first binaural beat when the first cognitive state is determined.

Example 25 includes the method of Example 19, and also includes automatically presenting a selected one of the first binaural beat or the second binaural beat based on a subsequent detection of the first cognitive state.

Example 26 includes the method of Example 24 or 25, and also includes pausing a game to change the cognitive state of the user.

Example 27 includes the method of any of Examples 19-22, 24, or 25, and also includes determining a third binaural beat to present to the user to change the cognitive state of the user to the first cognitive state or a third cognitive state after a period of time in the second cognitive state.

Example 28 is a non-transitory computer readable storage medium comprising computer readable instructions that, when executed, cause one or more processors to, at least gather first electroencephalographic data from the user, determine a first cognitive state of the user based on the first electroencephalographic data, determine a first binaural beat to present to the user based on the first cognitive and a second cognitive state, and present the first binaural beat to the user. The example instructions further cause the one or more processors to at least gather second electroencephalographic data from the user exposed to the first binaural beat, determine a first effectiveness of the first binaural beat to place the user in the second cognitive state, determine a second binaural beat to present to the user based on the first cognitive state, the second cognitive state, and the second electroencephalographic data, and present the second binaural beat to the user. In addition, the example instructions cause the one or more processors to at least determine a second effectiveness of the second binaural beat to place the user in the second cognitive state, perform a comparison of the first effectiveness and the second effectiveness, and select one of the first binaural beat or the second binaural beat for future presentation to the user to change the user cognitive state to the second cognitive state based on the comparison.

Example 29 includes the storage medium and instructions of Example 28, wherein the computer readable instructions, when executed, further cause the processor to present a first frequency to a first ear of the user via a first speaker and present a second frequency to a second ear of the user via a second speaker, the first binaural beat being a difference between the first frequency and the second frequency.

Example 30 includes the storage medium and instructions of Example 29, wherein the computer readable instructions, when executed, further cause the processor to present a third frequency to the first ear of the user via the first speaker, the second binaural beat being a difference between the third frequency and the second frequency.

Example 31 includes the storage medium and instructions of Example 29, wherein the computer readable instructions, when executed, further cause the processor to present a third frequency to the first ear of the user via the first speaker and present a fourth frequency to the second ear of the user via the second speaker, the second binaural beat being a difference between the third frequency and the fourth frequency.

Example 32 includes the storage medium and instructions of any of Examples 28-31, wherein the computer readable instructions, when executed, further cause the processor to present a video concurrently with at least one of the first binaural beat or the second binaural beat.

Example 33 includes the storage medium and instructions of Example 28, wherein the computer readable instructions, when executed, further cause the processor to automatically present the first binaural beat when the first cognitive state is determined.

Example 34 includes the storage medium and instructions of Example 28, wherein the computer readable instructions, when executed, further cause the processor to automatically present a selected one of the first binaural beat or the second binaural beat based on a subsequent detection of the first cognitive state.

Example 35 includes the storage medium and instructions of Examples 33 or 34, wherein the computer readable instructions, when executed, further cause the processor to pause a game to change the cognitive state of the user.

Example 36 includes the storage medium and instructions of any of Examples 28-31, 33, or 34, wherein the computer readable instructions, when executed, further cause the processor to determine a third binaural beat to present to the user to change the cognitive state of the user to the first cognitive state or a third cognitive state after a period of time in the second cognitive state.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A system to change a cognitive state of a user, the system comprising:
   a sensor to gather first electroencephalographic data from the user;
   an analyzer to determine a first cognitive state of the user based on the first electroencephalographic data, and to determine a first binaural beat to present to the user based on the first cognitive state and a second cognitive state; and
   an output to present the first binaural beat to the user, the first binaural beat being a difference between a first frequency presented to a first ear of the user and a second frequency presented to a second ear of the user;
   the sensor to gather second electroencephalographic data from the user exposed to the first binaural beat;
   the analyzer to determine a first effectiveness of the first binaural beat to place the user in the second cognitive state, and to determine a second binaural beat to present to the user based on the first cognitive state, the second cognitive state, and the second electroencephalographic data;
   the output to present the second binaural beat to the user, the second binaural beat being a difference between a third frequency presented to the first ear of the user and the second frequency presented to the second ear of the user; and the analyzer to determine a second effectiveness of the second binaural beat to place the user in the second cognitive state, to perform a comparison of the first effectiveness and the second effectiveness, and to select one of the first binaural beat or the second binaural beat for future presentation to the user to change the cognitive state of the user to the second cognitive state based on the comparison.

2. The system of claim 1, wherein the output includes a first speaker.

3. The system of claim 1, wherein the output includes a display to present a video concurrently with at least one of the first binaural beat or the second binaural beat.

4. The system of claim 1, wherein the analyzer is to cause the output to automatically present the first binaural beat when the first cognitive state is determined.

5. The system of claim 4, wherein the analyzer is to pause a game to change the cognitive state of the user.

6. The system of claim 1, wherein the analyzer is to cause the output to automatically present a selected one of the first binaural beat or the second binaural beat based on a subsequent detection of the first cognitive state.

7. The system of claim 1, wherein the analyzer is to determine a third binaural beat to present to the user to change the cognitive state of the user to the first cognitive state or a third cognitive state after a period of time in the second cognitive state.

8. The system of claim 7, wherein the output is to present a third frequency to the first ear of the user and to present a fourth frequency to the second ear of the user, the third binaural beat being a difference between the third frequency and the fourth frequency.

9. A system to change a cognitive state of a user, the system comprising:
  means for gathering first electroencephalographic data from the user;
  means for analyzing data to determine a first cognitive state of the user based on the first electroencephalographic data, and to determine a first binaural beat to present to the user based on the first cognitive and a second cognitive state;
  means for presenting the first binaural beat to the user; and
  means for determining a duration of time in the first cognitive state and the second cognitive state;
  the means for gathering to gather second electroencephalographic data from the user exposed to the first binaural beat;
  the means for analyzing to determine a first effectiveness of the first binaural beat to place the user in the second cognitive state, and to determine a second binaural beat to present to the user based on the first cognitive state, the second cognitive state, and the second electroencephalographic data;
  the means for presenting to present the second binaural beat to the user; and
  the means for analyzing to:
    determine a second effectiveness of the second binaural beat to place the user in the second cognitive state,
    perform a comparison of the first effectiveness and the second effectiveness,
    select one of the first binaural beat or the second binaural beat for future presentation to the user to change the user cognitive state to the second cognitive state based on the comparison, and
    determine a third binaural beat to present to the user to change the cognitive state of the user to the first cognitive state or a third cognitive state based on the duration of time in the second cognitive state.

10. The system of claim 9, wherein the means for presenting includes a first speaker to present a first frequency to a first ear of the user and a second speaker to present a second frequency to a second ear of the user, the first binaural beat being a difference between the first frequency and the second frequency.

11. The system of claim 10, wherein the first speaker is to present a third frequency to the first ear of the user, the second binaural beat being a difference between the third frequency and the second frequency.

12. The system of claim 10, wherein the first speaker is to present a third frequency to the first ear of the user and the second speaker is to present a fourth frequency to the second ear of the user, the second binaural beat being a difference between the third frequency and the fourth frequency.

13. The system of claim 9, wherein the means for analyzing is to cause the means for presenting to automatically present the first binaural beat when the first cognitive state is determined.

14. The system of claim 13, wherein the means for analyzing is to pause a game to change the cognitive state of the user.

15. The system of claim 9, wherein the means for analyzing is to determine a third binaural beat to present to the user to change the cognitive state of the user to the first cognitive state or a third cognitive state after a period of time in the second cognitive state.

16. The system of claim 9, wherein the means for presenting includes a display to present a video concurrently with at least one of the first binaural beat or the second binaural beat.

17. The system of claim 9, wherein the means for analyzing is to cause the means for presenting to automatically present a selected one of the first binaural beat or the second binaural beat based on a subsequent detection of the first cognitive state.

18. A system to change a cognitive state of a user, the system comprising:
  a sensor to gather first electroencephalographic data from the user;
  an analyzer to determine a first cognitive state of the user based on the first electroencephalographic data, and to determine a first binaural beat to present to the user based on the first cognitive state and a second cognitive state; and
  an output to present the first binaural beat to the user at a first point in time;
  the sensor to gather second electroencephalographic data from the user exposed to the first binaural beat;
  the analyzer to determine a first effectiveness of the first binaural beat to place the user in the second cognitive state, and to determine a second binaural beat to present to the user based on the first cognitive state, the second cognitive state, and the second electroencephalographic data;
  the output to present the second binaural beat to the user at a second point in time; and
  the analyzer to:
    determine a second effectiveness of the second binaural beat to place the user in the second cognitive state,
    perform a comparison of the first effectiveness and the second effectiveness,
    select one of the first binaural beat or the second binaural beat for presentation to the user at a third point in time to change the cognitive state of the user to the second cognitive state based on the comparison, and pause a visual presentation at the third point in time during the change of the cognitive state.

* * * * *